(12) United States Patent
Tanner et al.

(10) Patent No.: US 9,546,358 B2
(45) Date of Patent: Jan. 17, 2017

(54) COMPOSITIONS AND METHODS FOR REDUCING BACKGROUND DNA AMPLIFICATION

(71) Applicant: New England Biolabs, Inc., Ipswich, MA (US)

(72) Inventors: Nathan Tanner, Peabody, MA (US); Thomas C. Evans, Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 238 days.

(21) Appl. No.: 13/799,463

(22) Filed: Mar. 13, 2013

(65) Prior Publication Data

US 2013/0323793 A1    Dec. 5, 2013

Related U.S. Application Data

(60) Provisional application No. 61/655,033, filed on Jun. 4, 2012.

(51) Int. Cl.
 *C12N 9/12* (2006.01)
 *C12Q 1/68* (2006.01)
(52) U.S. Cl.
 CPC ........... *C12N 9/1241* (2013.01); *C12Q 1/6848* (2013.01)

(58) Field of Classification Search
None
See application file for complete search history.

(56) References Cited

U.S. PATENT DOCUMENTS

2006/0141491 A1* 6/2006 Chakrabarti et al. ............. 435/6
2008/0009420 A1* 1/2008 Schroth et al. ................ 506/16

OTHER PUBLICATIONS

Paulin et al. (1998) Nucl. Acids. Res. vol. 26 No. 21 5009-5010.*
Tanner, et al., BioTechniques, 53:81-89 (2012).
Nagamine, et al., Molecular and Cellular Probes, 16:223-229 (2002).

\* cited by examiner

*Primary Examiner* — Suchira Pande
(74) *Attorney, Agent, or Firm* — New England Biolabs, Inc.; Harriet M. Strimpel

(57) ABSTRACT

Compositions are provided that include a plurality of small molecules selected from the group consisting of an amide, urea or acetone having a molecular weight less than 300 g/mol; and dNTPs and a polymerase in a buffer suitable for use as an amplification buffer. Methods of use of the compositions are also described for reducing non-template DNA amplification.

8 Claims, 8 Drawing Sheets

COMPOSITIONS AND METHODS FOR REDUCING BACKGROUND DNA AMPLIFICATION

CROSS REFERENCE

This application claims right of priority to provisional patent application serial number U.S. 61/655,033 filed Jun. 4, 2012.

BACKGROUND

DNA amplification is frequently used in DNA diagnostic tests and sequencing protocols. Both require a low background of non-specific amplification. Unfortunately, amplification methods that utilize primers appear to give rise to false positive signals of non-template DNA that affect the quality of the results. These positive signals can be detected in control samples with non-template DNA or no DNA. Without wishing to be limited by theory, it is believed that false positives predominantly result from transient primer secondary structure formation and primer dimers.

Improvements in amplification signal and amplification specificity have not removed the adverse effects of background signal for isothermal amplification reactions. Chakrabati, et al., *Nucleic Acids Research*, 29:2377-2381 (2001), described enhancement of polymerase chain reaction (PCR) amplification using single low molecular weight amide additives, in particular, 0.5% to 7.5% formamide, N-hydroxyethylpyrrolidone or 2-pyrroliidone. Isobutyramide or N-methylacetamide were found to be less desirable as PCR amplification enhancers.

SUMMARY

In general, a composition is provided that includes a plurality of small molecules selected from the group consisting of an amide, urea or acetone having a molecular weight less than 300 g/mol; and dNTPs and a polymerase in a buffer suitable for use as an amplification buffer.

In one aspect, the plurality of small molecules includes a mixture of N-alkylcarboxamide and carboxamide. For example, the carboxamide is at a concentration of 0.02 M-0.7 M and N-alkyl carboxamide is at a concentration of 0.03 M-1.5 M. For example, the carboxamide and the N-alkyl carboxamide is combined at a ratio of 1:1 to 1:4.

In another aspect, the plurality of small molecules are two or more small molecules selected from the group consisting of isobutyramide and N-methylformamide; propionamide and N-methylformamide; valeramide and N-methylformamide; isobutyramide and N,N-diethylformamide; and valeramide and N,N-diethylformamide where the two or more small molecules act synergistically to substantially reduce background non-specific amplification.

In general, a method is provided that includes adding to a reaction vessel, a mixture of at least two small molecule reagents that act synergistically to inhibit amplification of non-template nucleic acids, wherein the reaction vessel further includes a buffer suitable for DNA amplification, a template nucleic acid, a DNA polymerase and one or more primers; and inhibiting amplification of a non-template nucleic acid.

In one aspect, the method utilizes a plurality of small molecule reagents including a pair of small molecules selected from the group consisting of isobutyramide and N-methylformamide; or propionamide and N-methylformamide; or valeramide and N-methylformamide; or isobutyramide and N,N-diethylformamide; or valeramide and N,N-diethylformamide.

BRIEF DESCRIPTION OF THE FIGURES

Additives shown are:
FIG. 2A shows the effect of 0.7 M N-methylformamide on target and non-specific amplification;
FIG. 2B shows the effect of 1.1 M N-methylformamide on target and non-specific amplification; and
FIG. 2C shows the effect of 0.4 M isobutyramide on target and non-specific amplification.

Without the addition of chemical additives, robust positive amplification is seen at all temperatures (black solid lines), but undesired non-template amplification is also observed below 72° C. (black dashed lines). The presence of a single additive increases the time interval required to detect non-template amplification (grey dashed lines) in the temperature range of 65° C.-68° C., but the additives were unable to reduce non-template amplification below 65° C. The target amplification reaction in the presence of additive and template (grey solid lines) was not significantly affected at lower temperatures by the presence of single additives, but was inhibited at higher temperatures. Increasing the amounts of isobutyramide or N-methylformamide above 0.4 M and 1.0 M respectively did not affect the non-template amplification at lower temperature and served only to further inhibit the target amplification whereas 1.1 M N-methylformamide inhibited target amplification above 68° C. These outcomes preclude the use of single additives at all temperatures desired for LAMP reactions.

Figure 3:
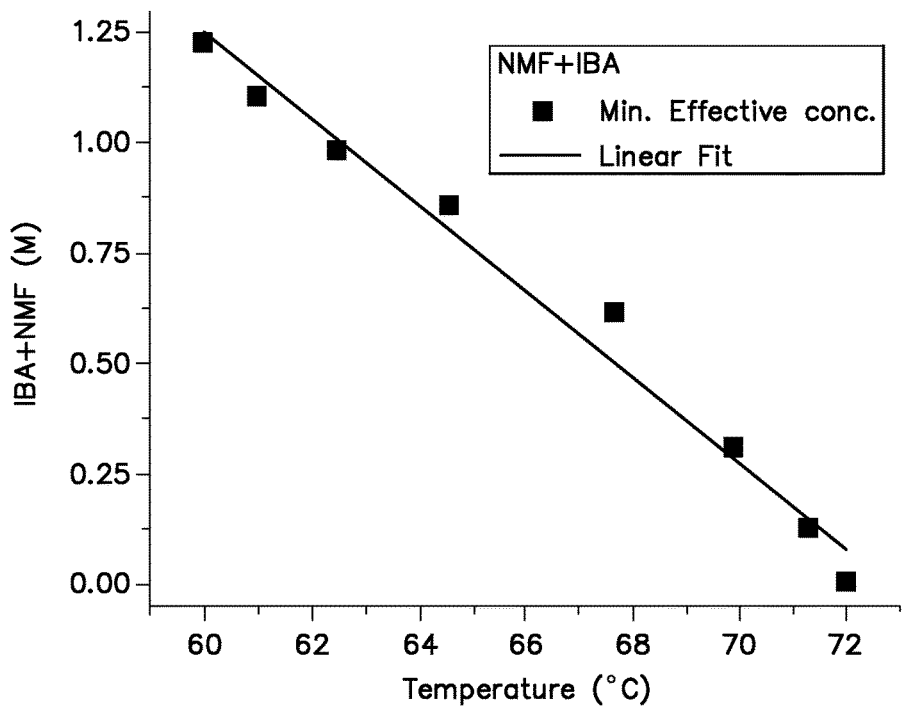

FIG. 3 shows that the amount of a mixture of additives for substantially complete suppression of background is proportional to temperature. Here a mixture of 1.7 M isobutyramide and 3.2 M N-methylformamide was added to a 25 µl LAMP reaction mixture and the minimum effective molar amount to achieve substantially complete suppression of background was determined (y-axis) at different temperatures plotted vs. temperature (X-axis). The plotted data showed a strong linear correlation of suppression with temperature. The resulting equation prescribed conditions for successful elimination of non-template amplification ($y=-0.09702x+7.0663$, $R^2=0.98$). This is described in more detail in Example 1.

Figure 4:
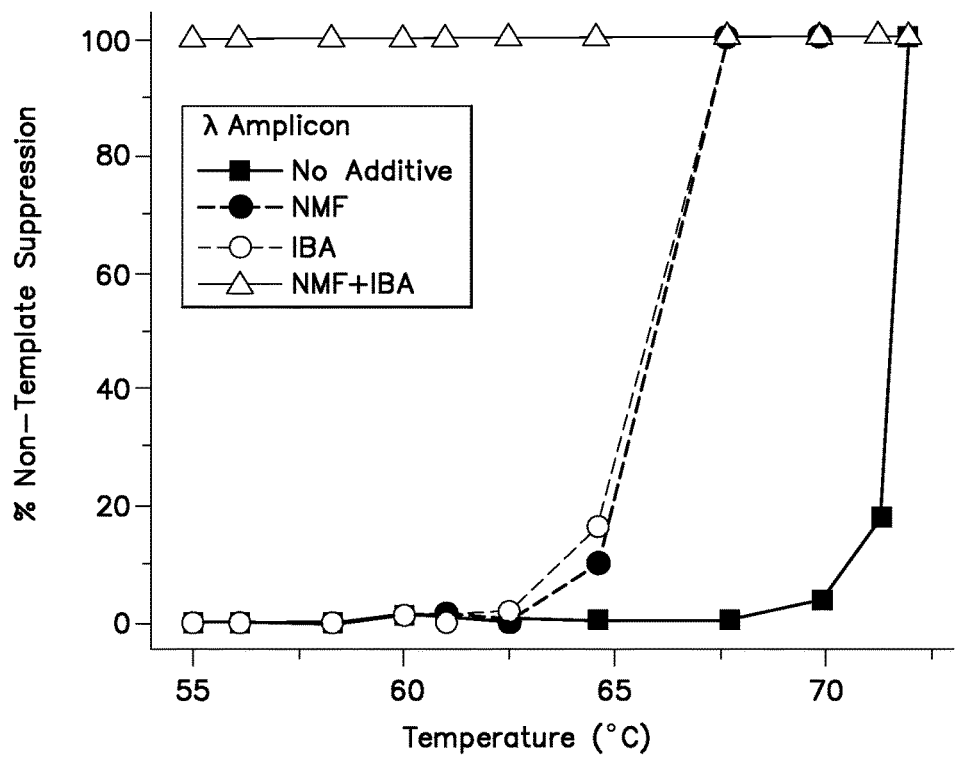

FIG. 4 shows the synergistic effect of two additives. Data is graphed as percent suppression of non-template amplification on the y-axis against LAMP reaction temperature on the x-axis (calculated as described in Example 1). The black solid line corresponds to an absence of any small molecule additive; black and grey dashed lines represent the presence of a single small molecule additive, N-methylformamide and isobutyramide, respectively; and grey solid line represents a mixture of N-methylformamide and isobutyramide. In the presence of the two small molecule additives, non-template amplification suppression was achieved at all temperatures tested, and a synergistic effect was observed at moderate to lower temperatures.

Figure 5A:
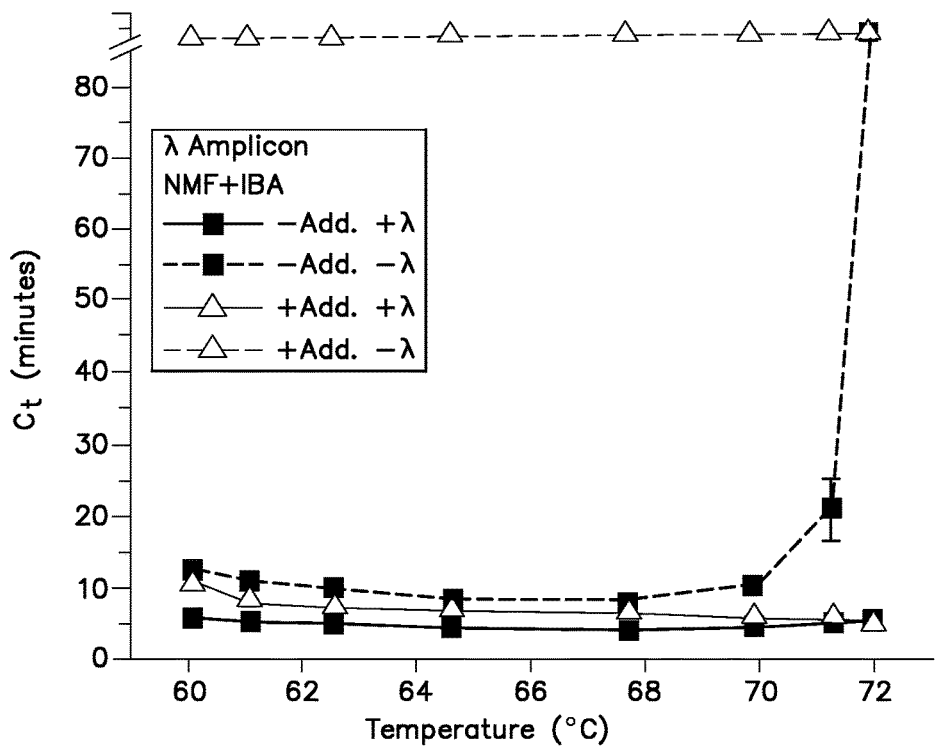
Figure 5B:
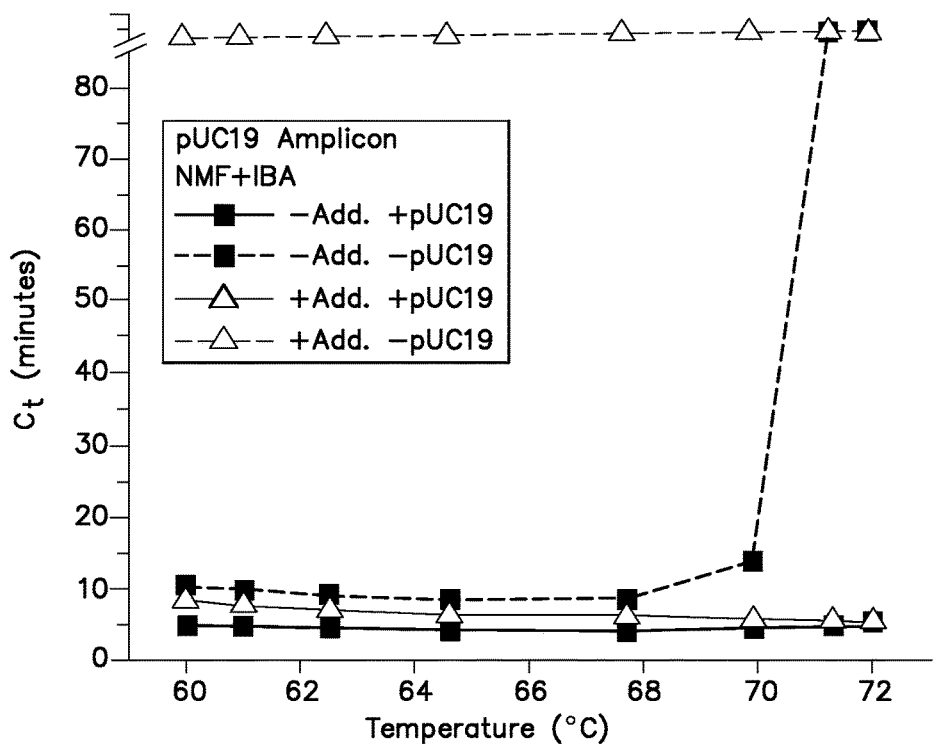
Figure 5C:
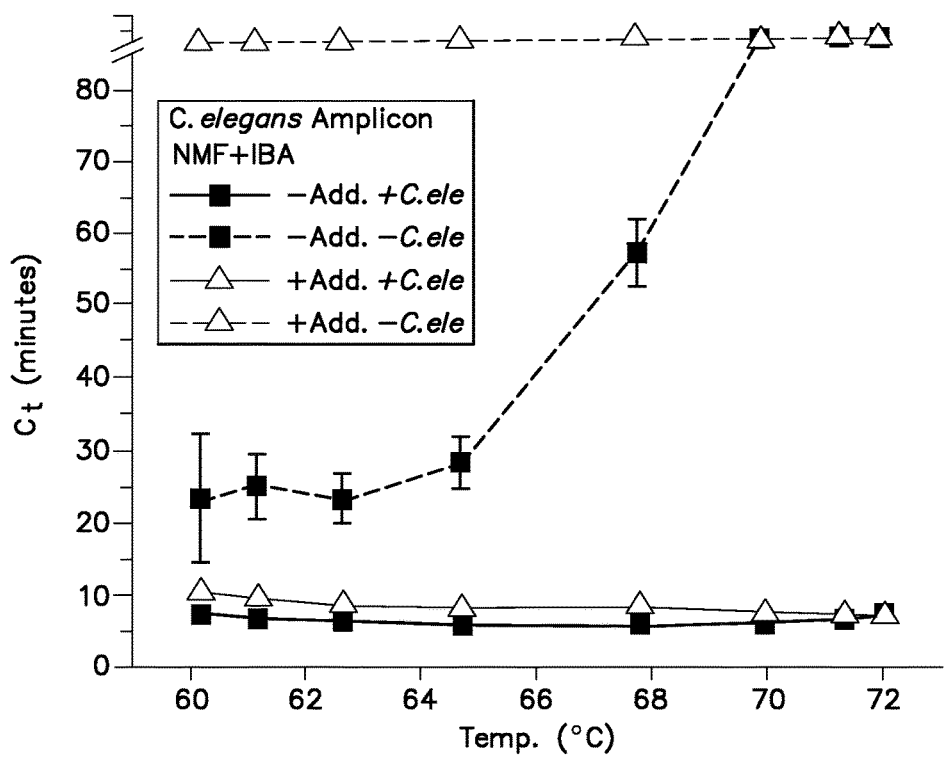
Figure 5D:
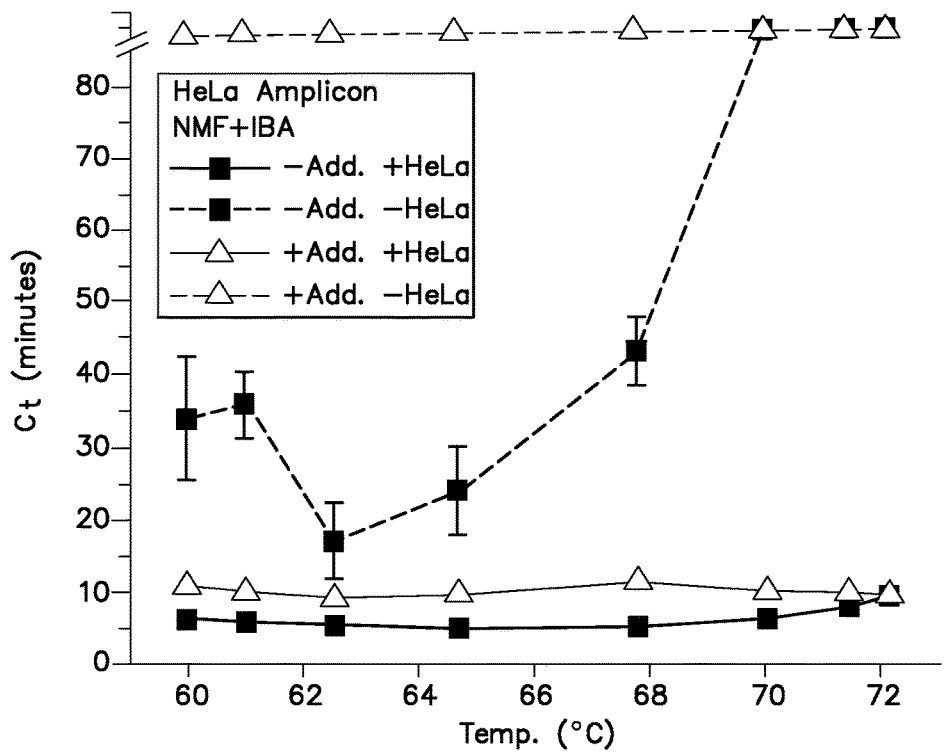

FIG. 5A-D shows that the synergistic effect of an additive mixture is independent of the sequence of LAMP primers and template DNAs. Time to threshold ($C_t$) is plotted on the y-axis against reaction temperature on the x-axis. A $C_t$ time of >85 minutes indicates that no amplification signal was detected, but a data point is plotted after y-axis break as maximum reaction time. Reaction conditions depicted are: without additive (black squares), with additive (grey triangles), with template DNA (solid line) and without template DNA (dashed line). Data is from four LAMP primer and template DNA sets:

FIG. 5A shows the effect of an additive mixture on lambda amplicon, A phage target DNA;

FIG. 5B shows the effect of an additive mixture on AmpR amplicon, pUC19 target DNA;

FIG. 5C shows the effect of an additive mixture on lec-10 amplicon, C. elegans target DNA; and FIG. 5D shows the effect of an additive mixture on BRCA1 amplicon, HeLa target DNA.

A beneficial effect was observed for all amplicons tested where a dramatic decrease in background amplification product was observed at all temperatures in the presence of two additives and no template (grey dashed lines). The level of non-template amplification varied between the primer sets, with some producing no background amplification at 70° C. No deleterious effect from the small molecule additives was seen on target amplification, while the additives successfully inhibited non-template amplification for all samples at lower temperatures.

FIG. 6A-D shows that the synergistic effect of using different mixtures of additives on eliminating non-target background amplification is absent with single additives.

Time to threshold ($C_t$) is plotted on the y-axis against amount of additive on the x-axis. The additive volume was either a single additive alone (black squares) or a mixture of two additives (grey triangles).

Figure 6A:
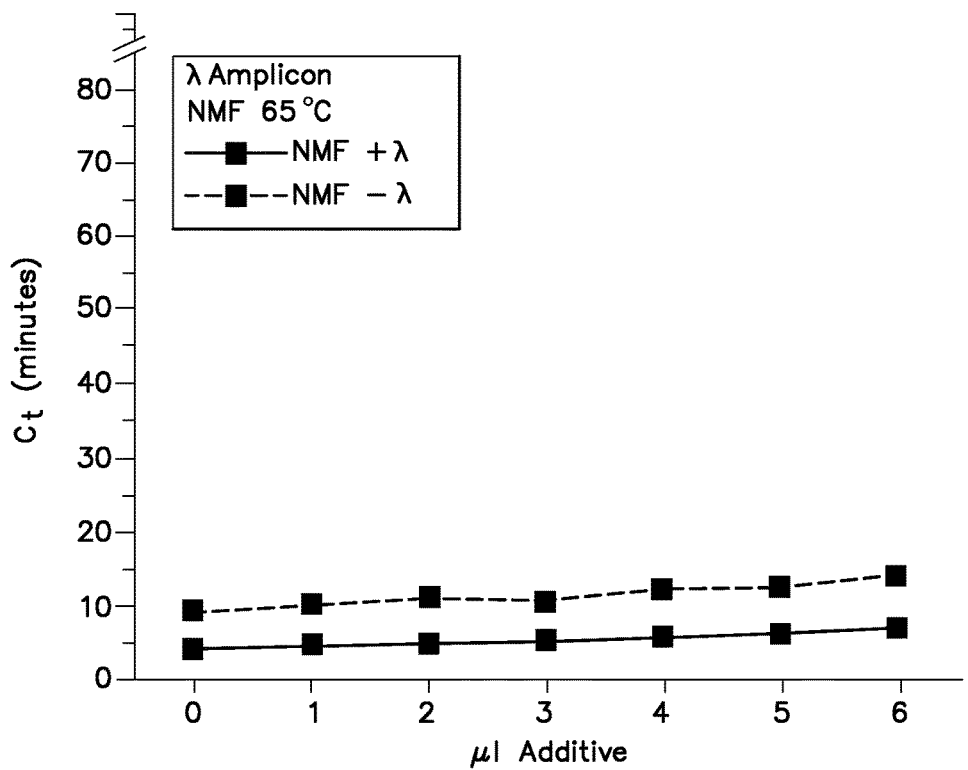

FIG. 6A shows the effect of increasing amounts of 3.2 M N-methylformamide with no beneficial effect observed.

Figure 6B:
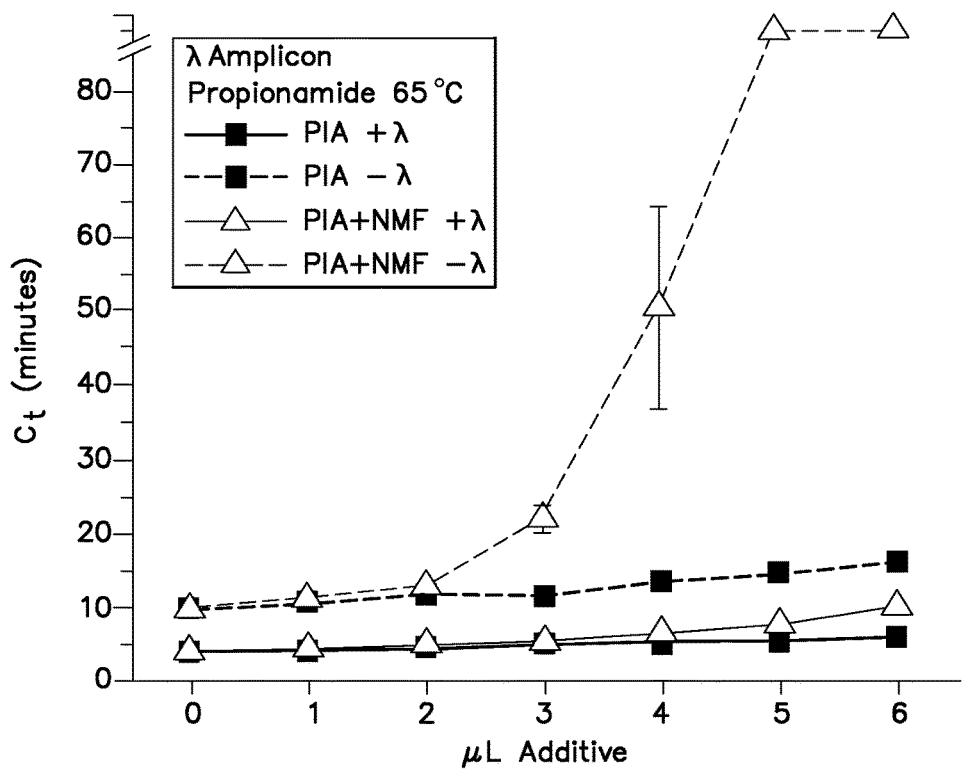

FIG. 6B shows the effect of increasing amounts of 1.7 M propionamide with no beneficial effect observed.

Figure 6C:
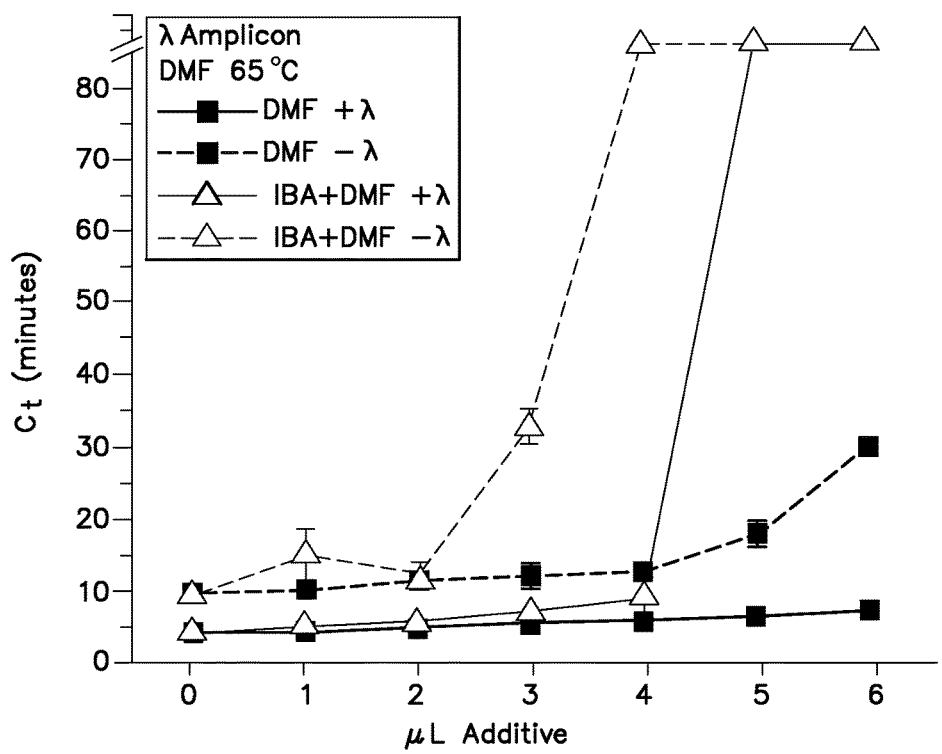

When 1.7 M propionamide mixed with 3.2 M N-methylformamide (grey triangles), non-template reduction was observed at concentrations lower than the additive concentrations of the individual compounds. This synergistic effect is also shown for:

FIG. 6C 3.2 M N,N-dimethylformamide mixed with 1.7 M isobutyramide, and

Figure 6D:
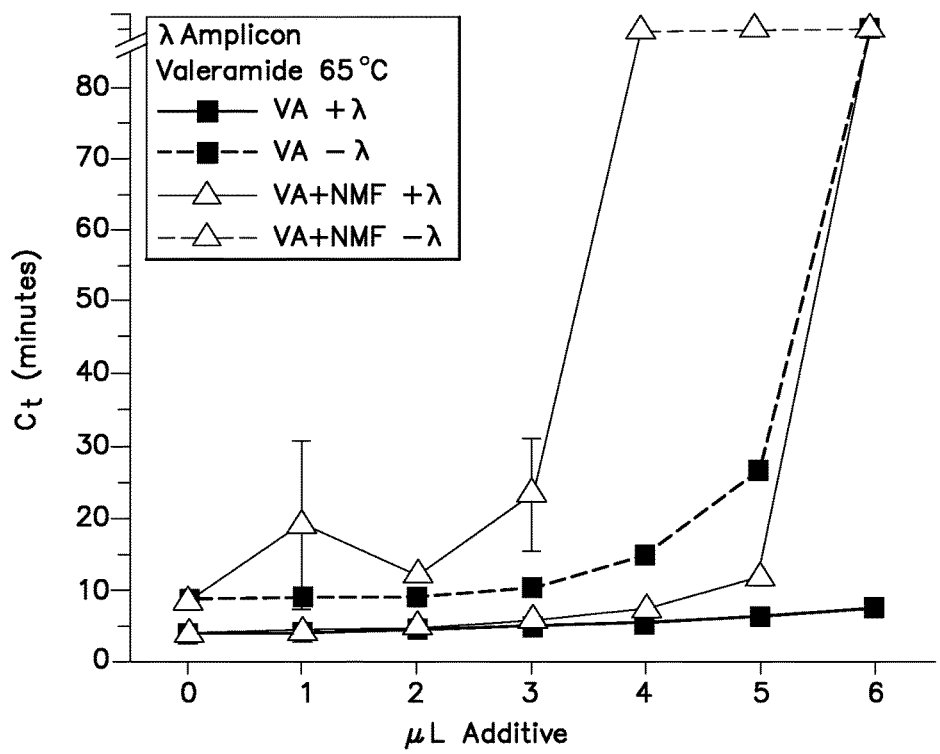

FIG. 6D 0.85 M valeramide and 3.2 M N-methylformamide.

Details of concentrations of the additives and the synergistic effect on reducing background are shown in Table 2.

DETAILED DESCRIPTION OF EMBODIMENTS

A plurality of small molecules mixed together resulted in a surprising synergistic effect on removal of detectable amplification of non-template polynucleotide including DNA or RNA with no inherent limit on types of target sequences. This synergistic effect was observed at the temperature suitable for amplification of target sequences although, used individually, the same small molecules were unable to prevent non-template amplification. High concentrations of individual small molecules inhibited amplification of template DNA (see for example, FIG. 4, Table 2).

Figure 1:
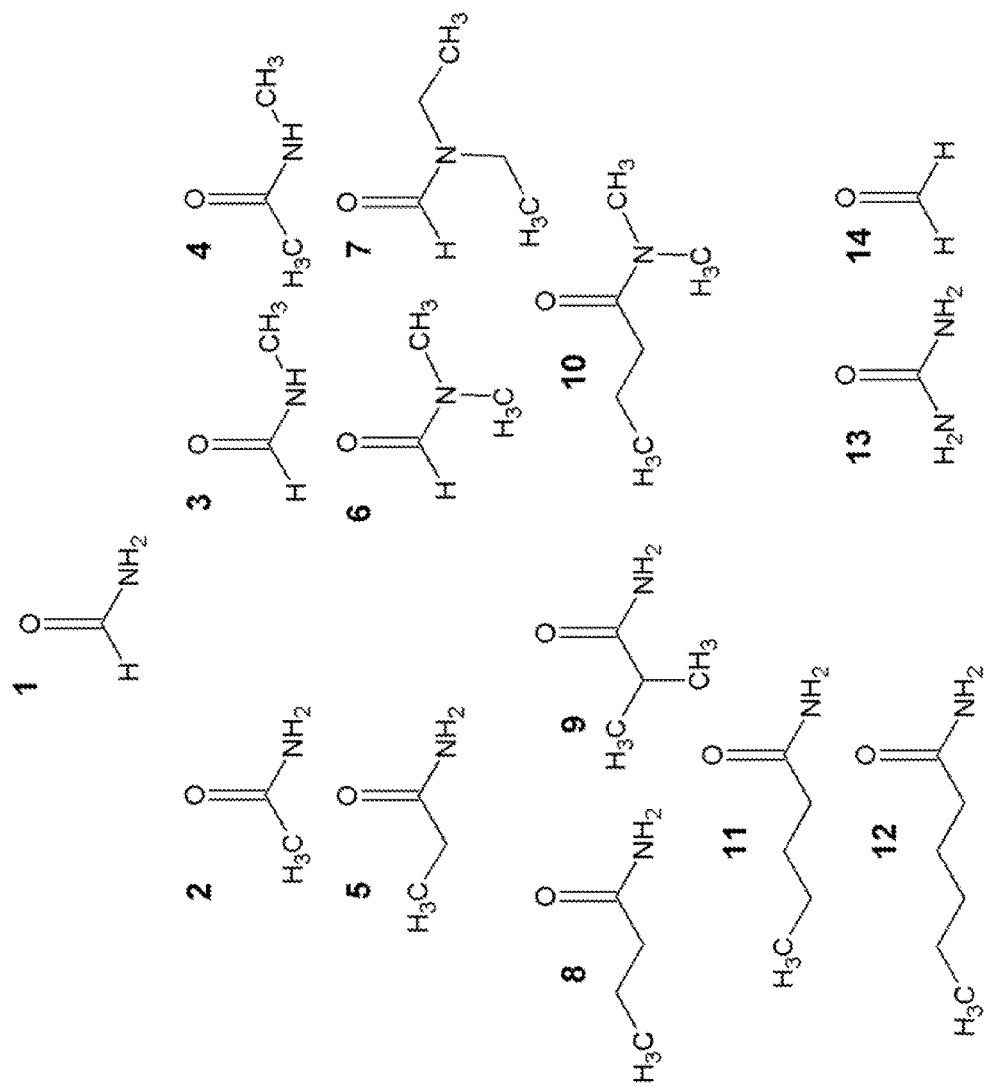
FIG. 1 shows examples of additives that cause reduction in background in amplification reactions. The additives shown are:
1) formamide (FA);
2) acetamide, (AA);
3) N-methylformamide (NMF);
4) N-methylacetamide (NMA);
5) propionamide (PIA);
6) N,N-dimethylformamide (DMF);
7) N,N-diethylformamide (DEF);
8) butyramide (BA);
9) isobutyramide (IBA);
10) N,N-dimethylbutyramide (DMB);
11) valeramide (VA);
12) hexanamide, (HA);
13) urea (U);
14) acetone (A).
Figure 2A:
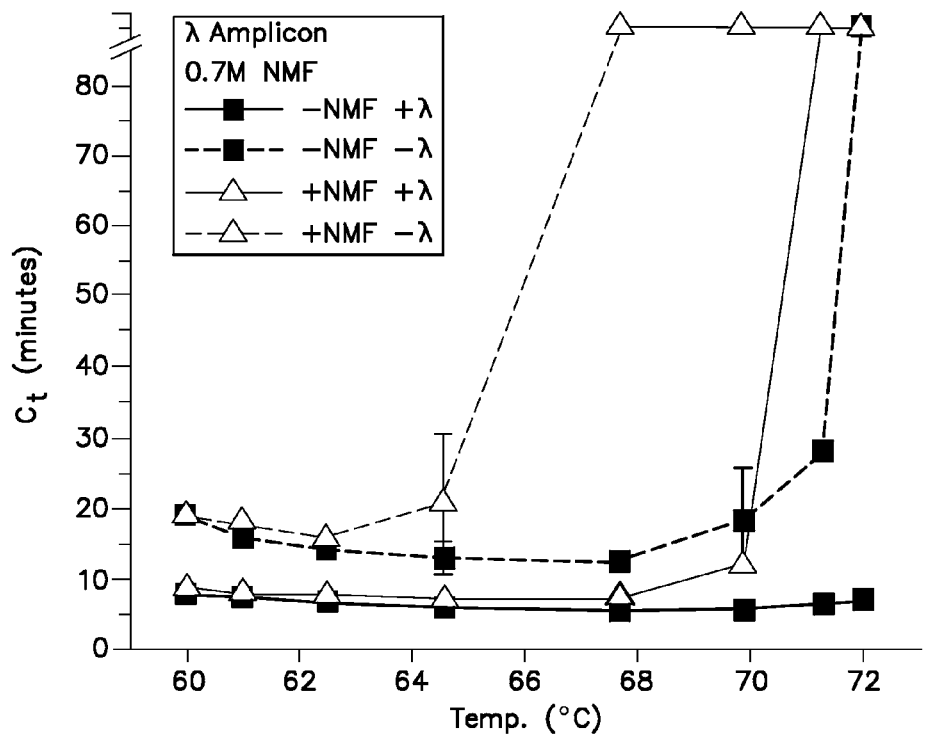
FIG. 2A-C shows that single additives are not effective in removal of background signal in Loop-Mediated Isothermal Amplification (LAMP). The time to threshold ($C_t$) for detecting an amplification product from lambda DNA is plotted on the y-axis against temperature in degrees centigrade on the x-axis. The threshold time for positive (with template) reactions occurs rapidly while the negative (non-template) reactions do not produce a threshold time. As graphed, a $C_t$ time of >85 minutes indicates that no amplification signal was detected, but a data point is plotted after y-axis break as maximum reaction time for clarity. Reaction conditions depicted are: without additive (black squares), with additive (grey triangles), with template A DNA (solid line) and without template DNA (dashed line).
Figure 2B:
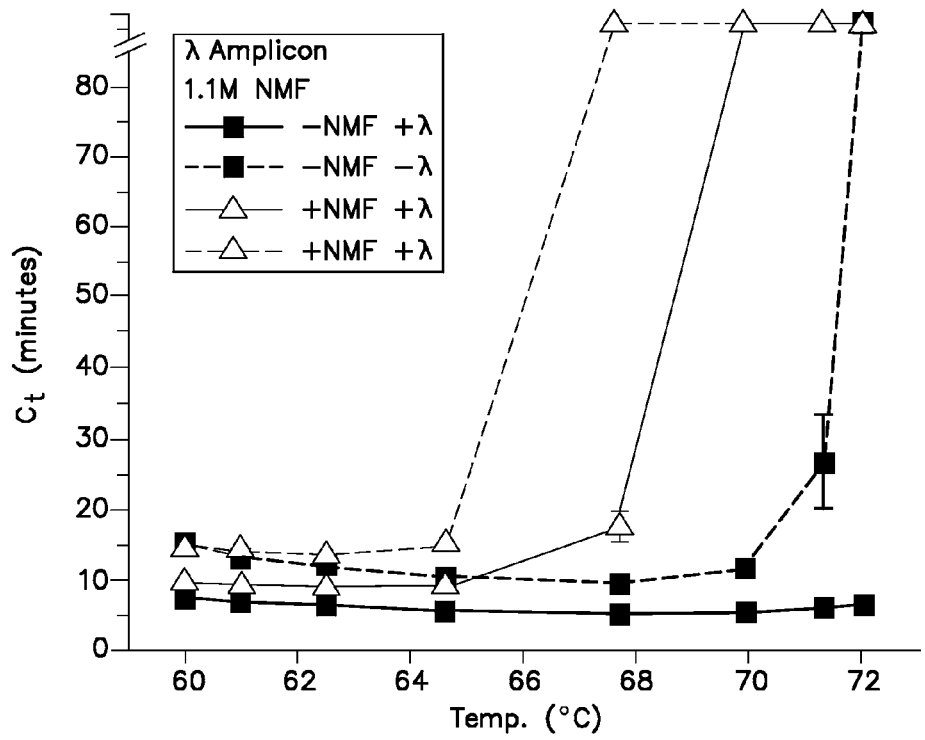
Figure 2C:
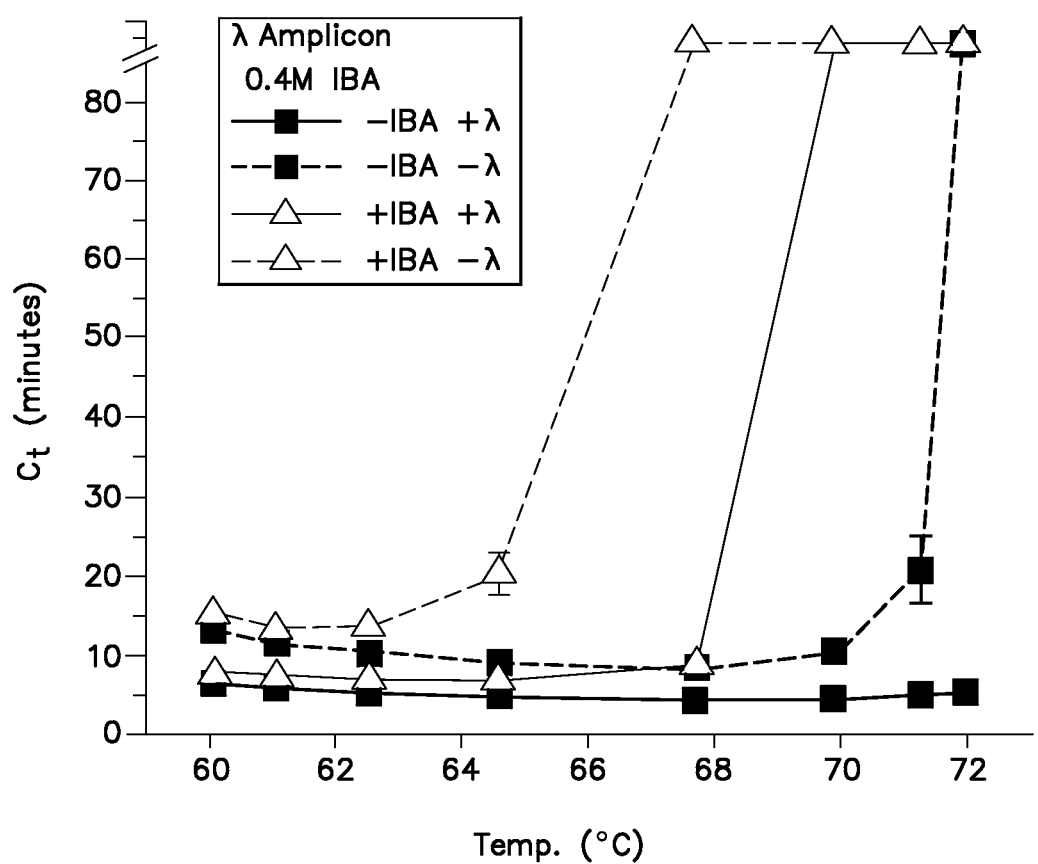

Examples of small molecules for use in mixtures to reduce non-template amplification reactions are shown in FIG. 1 and are characterized by a molecular weight of less than 500 g/mol for example, less than 400 g/mol for example less than 300 g/mol, for example less than 200 g/mol for example less than 150 g/mol. A mixture of small molecules when added to an isothermal amplification reaction resulted in a synergistic effect (greater than the effect of using the small molecules separately), exemplified by a mixture of a carboxamide (formamide; acetamide; propionamide; butyramide or isobutryamide; valeramide; hexanamide) mixed with an N-alkyl carboxamide (N-methylformamide; N-methylacetamide; N,N-dimethylformamide; N,N-diethylformamide; N,N-dimethylbutyramide).

Any amplification procedure may experience non-template amplification, particularly in real-time quantitative methods. Mixtures as described herein can synergistically eliminate undesired amplification resulting from, for example, amplification of non-template primers and adapters including hairpin primers, DARQ probes (Tanner et al., *BioTechniques*, 53:81-89 (2012)), and linear primers. Mixtures of additives may be added to any amplification reaction, including for example, isothermal amplification protocols including strand displacement amplification (SDA), LAMP, helicase dependent amplification (HDA), and rolling circle amplification or non-isothermal methods, e.g. PCR.

This synergistic effect was observed for Family A or Family B polymerases in the amplification reaction. For example, the synergistic mixtures were effective in amplifications using Bst, Bst 2.0 (NEB, Ipswich, Mass.), and PolD (mutant 9° N), and further including chimeric polymerases comprising a polymerase domain and a DNA binding domain from different sources such as Bst 2.0-Sso7d, PolD Sso7d (PolD2), KOD and variants of polymerases alone or fused to Sso7d, and Tgo Sso7d.

The synergistic effect of mixtures of additives were also observed for different sized template sequences and for various template sequences contained in longer DNAs from plasmid, viral DNA prokaryotic and eukaryotic DNA. Reactions were performed in standard polymerase buffers at pH 7.5-pH 10, and containing 10 mM-150 mM KCl. For LAMP, temperatures of 55° C.-72° C. were applied and the plurality of small molecule additives were found to effectively inhibit the non-template amplification.

All references cited herein are incorporated by reference.

EXAMPLES

Example 1

LAMP Assay 0.4-8 ng/μl DNA polymerase (Bst 2.0-Sso7d) in LAMP Buffer [20 mM Tris, 125 mM KCl, 10 mM $(NH_4)_2SO_4$, 8 mM $MgSO_4$, 1.4 mM dNTPs, 0.1% Tween-20® (Sigma-Aldrich, St. Louis, Mo.), pH 8.8 25° C.]

1.6 μM Forward internal primer (FIP)/Back internal primer (BIP), 0.2 μM F3/B3, 0.4 μM LoopF/LoopB 5 ng λ DNA or none (non-template control) per reaction (25 μl)

The additive solution was added to the amplification mixture to provide a final concentration in the range of 0-40% v/v where the stock solution of additive was solubilized in water. For example, concentrations of isobutyramide in the range of 0.005 M-1.5 M, 0.01 M-1.2 M, or 0.01 M-0.7 M and N-methylformamide in the range of 0.01-2 M, 0.02 M-1.5 M, or 0.02 M-1 M (combined for example, at ratios of 10:1, 8:1, 6:1, 4:1, 2:1, 1.8:1, 1.6:1, 1.4:1, 1.2:1, 1:1 of N-methylformamide:isobutyramide) were tested at various temperatures. Other examples included in the final reaction mixture 0.02 M-1.3 M propionamide, 0.2 M-2 M Urea, 0.1 M-3.8 M formamide, 0.05 M-2 M acetamide, 0.02 M-0.5 M valeramide, 0.01 M-2 M N,N-dimethylformamide, 0.01 M-2 M N,N-diethylformamide, 0.01 M-1.8 M N,N-dimethylbutyramide.

The extent of amplification of lambda DNA (unless otherwise specified) with a LAMP amplicon size of 100-200 bases was measured by real-time fluorescence using 2 μM SYTO-9® (Life Technologies, Carlsbad, Calif.) double strand DNA intercalating dye (Nagamine, et al., *Molecular and Cellular Probes*, 16:223-229 (2002)) using the following primers:

```
Lambda Primers
FIP:
                                         (SEQ ID NO: 1)
CAGCCAGCCGCAGCACGTTCGCTCATAGGAGATATGGTAGAGCCGC BIP:
                                         (SEQ ID NO: 2)
GAGAGAATTTGTACCACCTCCCACCGGGCACATAGCAGTCCTAGGGACAGT F3:
                                         (SEQ ID NO: 3)
GGCTTGGCTCTGCTAACACGTT B3:
                                         (SEQ ID NO: 4)
GGACGTTTGTAATGTCCGCTCC LoopF:
                                         (SEQ ID NO: 5)
CTGCATACGACGTGTCT LoopB:
                                         (SEQ ID NO: 6)
ACCATCTATGACTGTACGCC
```

The reduction in background fluorescence from non-template amplification was quantitatively assessed. The total reaction time for LAMP is 90 minutes. In the absence of additives, a positive signal for an amplification product of a template could be detected at about 3 minutes-15 minutes at temperatures 55° C.-72° C. and for a non-template signal at 8 minutes-30 minutes at temperatures below about 71° C. When a mixture of additives was included in the amplification mixture, a positive signal for template amplification is still seen at 3 minutes-15 minutes but no signal is seen even after 85 minutes for non-template reactions. This is recorded however as the maximum time to illustrate the synergistic effect. However, for convenience of graphing purpose, whenever the amplification signal did not appear after 90 minutes, it is marked as if amplification signal appeared at this time point even though there is no signal observed. Significantly, the results in FIGS. 3-5 and in Tables 1-2 show that increasing the amount of small molecules in the mixture can produce the optimum (zero) no template signal at each temperature tested. In all cases, the effect of the ratio of components of the mixture at specific molar concentrations is greater than the effect of each component small molecule individually tested at the same molar concentration and temperature (exemplified by data in Table 2).

The degree of suppression of non-template amplification (FIG. 4) was calculated as (additive threshold time)/(non-additive threshold time)*100-100 (for example, 11 minutes vs. 10 minutes=10% inhibition) normalized to 100% inhibition at total reaction time, typically 90 minutes to illustrate effects exclusive to non-template signal.

Determination of a Synergistic Effect of a Plurality of Additives

The minimum effective concentration of a single compound at which non-template amplification was completely suppressed (100%) at 65° C. was compared to a mixture of compounds. The synergistic effect of mixing a carboxamide and N-alkylcarboxamide was examined.

A mixture of 3.2 M N-methylformamide and 1.7 M isobutyramide was added in varying amounts at certain temperatures, with the minimum effective concentration determined to eliminate non-template amplification shown in Table 1 and FIG. 3. The linear regression analysis of FIG. 3 was converted to volume of the additive mixture vs. decrease in temperature prescribed addition of 0.5397 μL additive mix (25 μL reaction) per ° C. below 72° C. (see Table 1). This trend continues outside of the illustrated range, as amounts in Table 1 and FIG. 4 also demonstrate this linear relationship for temperatures below 60° C. Table 1 provides volume of the mix and total concentration (N-methylformamide+isobutyramide) and demonstrates the synergistic effect of combining these additives. For example, at 60° C., 0.4 M isobutyramide and 1.1 M N-methylformamide alone achieve ~1% suppression of non-template amplified using LAMP (see FIG. 4). When combined, the suppression of non-template amplification is 100% at that temperature, although the effective combined concentration is lower than even the added amounts of the compounds individually (1.5 M if non-synergistic, 1.2 M observed). At 65° C., the individual additives give ~10% suppression but 100% when mixed (1.5 M non-synergistic, 0.78 M observed). Additional examples of this synergistic effect are shown in Table 2, with all values reported representing the minimum effective concentration required for 100% suppression of non-template amplification at 65° C. The individual amounts listed were independently capable of suppression, but when mixed the synergistic effect was observed, and the values of single additive effective concentration and mixture effective concentration are compared. For example, 0.20 M valeramide and 0.26 M N,N-diethylformamide were capable of background suppression at this temperature. When combined, however, a total concentration of 0.12 M VA+DEF was effective. This synergistic effect enabled non-template amplification suppression at lower temperatures (to 55° C.) and use of substantially smaller amounts of the additives in the reaction mixture.

Mixtures were typically a 1.8× amount of Compound B relative to Compound A, except with valeramide (3.7×B:A), N,N-dimethylbutyramide (1.6×B:A), and formamide (0.3× B:A).

TABLE 1

Minimum effective concentration of N-methylformamide and isobutyramide mix required for suppression of non-template amplification at various temperatures

| Temperature | μL Mix | Conc. (M) | Conc. (% v/v) |
|---|---|---|---|
| 72 | 0 | 0 | 0 |
| 70 | 1.6 | 0.31 | 2.1 |
| 68 | 2.9 | 0.57 | 3.9 |
| 65 | 4.0 | 0.78 | 5.4 |
| 60 | 6.3 | 1.2 | 8.5 |
| 55 | 9 | 1.7 | 12.2 |

TABLE 2

Minimum effective concentration of additive mixtures compared to individual additives required for suppression of non-template amplification demonstrates synergistic effect

| Compound A | Conc. (M) | Compound B | Conc. (M) | Mix Conc. (M) |
|---|---|---|---|---|
| FA | 1.8 | NMF | 1.1 | 1.7 |
| PIA | 0.80 | NMF | 1.1 | 0.7 |
| IBA | 0.41 | NMF | 1.1 | 0.7 |
| VA | 0.20 | NMF | 1.1 | 0.6 |
| IBA | 0.41 | DMF | 0.77 | 0.6 |
| IBA | 0.41 | DEF | 0.26 | 0.29 |
| VA | 0.20 | DEF | 0.26 | 0.12 |
| DMB | 0.24 | DEF | 0.26 | 0.14 |

What is claimed is:

1. A method comprising:
   (a) producing a reaction mixture by combining:
      (i) a carboxamide selected from the group consisting of formamide, acetamide, propionamide, butyramide, isobutryamide, valeramide and hexanamide; and an N-alkylcarboxamide selected from the group consisting of N-methylformamide, N-methylacetamide, N,N-dimethylformamide, N,N-diethylformamide, N,N-dimethylbutyramide, at a molar ratio in the range of 1:1 to 1:10 (carboxymide:N-alkylcarboxamide),
      (ii) a polymerase;
      (iii) dNTPs;
      (iv) one or more primers;
      (v) template and non-template nucleic acid; and
      (vi) a DNA amplification buffer; and
   (b) incubating the reaction mixture under conditions to amplify the template nucleic acid, wherein the carboxamide and N-alkylcarboxamide synergistically reduce amplification of the non-template nucleic acid.

2. The method of claim 1, wherein the carboxamide is at a concentration in the range of 0.02 M to 0.7 M and the N-alkyl carboxamide is at a concentration in the range of 0.03 M to 1.5 M.

3. The method of claim 1, wherein the polymerase is a family A polymerase or a family B polymerase.

4. The method of claim 1, wherein the polymerase is selected from the group consisting of Bst polymerase, PolD polymerase, KOD polymerase, mutants of the same and chimeras of the same.

5. The method of claim 1, wherein the polymerase is a strand-displacing polymerase.

6. The method of claim 1, wherein the conditions of step (b) are isothermal.

7. The method of claim 1, wherein the conditions of step (b) comprise thermocycling.

8. The method of claim 1, wherein the reaction mixture comprises isobutryamide and N-methylformamide.

* * * * *

```
                      SEQUENCE LISTING

<160> NUMBER OF SEQ ID NOS: 6

<210> SEQ ID NO 1
<211> LENGTH: 46
<212> TYPE: DNA
<213> ORGANISM: Enterobacteria phage lambda

<400> SEQUENCE: 1
cagccagccg cagcacgttc gctcatagga gatatggtag agccgc              46

<210> SEQ ID NO 2
<211> LENGTH: 51
<212> TYPE: DNA
<213> ORGANISM: Enterobacteria phage lambda

<400> SEQUENCE: 2
gagagaattt gtaccacctc ccaccgggca catagcagtc ctagggacag t         51

<210> SEQ ID NO 3
<211> LENGTH: 22
<212> TYPE: DNA
<213> ORGANISM: Enterobacteria phage lambda

<400> SEQUENCE: 3
ggcttggctc tgctaacacg tt                                        22

<210> SEQ ID NO 4
<211> LENGTH: 22
<212> TYPE: DNA
<213> ORGANISM: Enterobacteria phage lambda

<400> SEQUENCE: 4
ggacgtttgt aatgtccgct cc                                        22

<210> SEQ ID NO 5
<211> LENGTH: 17
<212> TYPE: DNA
<213> ORGANISM: Enterobacteria phage lambda

<400> SEQUENCE: 5
ctgcatacga cgtgtct                                              17

<210> SEQ ID NO 6
<211> LENGTH: 20
```

```
<212> TYPE: DNA
<213> ORGANISM: Enterobacteria phage lambda

<400> SEQUENCE: 6
accatctatg actgtacgcc                                              20
```